(12) United States Patent
Elsener et al.

(10) Patent No.: US 7,829,028 B2
(45) Date of Patent: Nov. 9, 2010

(54) STORAGE UNIT AND TRANSFER SYSTEM FOR STORING AND PROVIDING BIOLOGICAL SAMPLES

(75) Inventors: Donat Elsener, Thun (CH); Dietmar Reisch, Thun (CH)

(73) Assignee: REMP AG, Oberdiessbach (CH)

( * ) Notice: Subject to any disclaimer, the term of this patent is extended or adjusted under 35 U.S.C. 154(b) by 925 days.

(21) Appl. No.: 11/680,045

(22) Filed: Feb. 28, 2007

(65) Prior Publication Data

US 2007/0205126 A1  Sep. 6, 2007

(30) Foreign Application Priority Data

Mar. 2, 2006  (CH) .................................. 00334/06

(51) Int. Cl.
*B01L 9/00* (2006.01)
*G05B 21/00* (2006.01)
*B65D 85/48* (2006.01)
*B65D 6/04* (2006.01)

(52) U.S. Cl. ................. 422/104; 206/263; 206/264; 206/456; 206/562; 700/266

(58) Field of Classification Search .............. 206/456
See application file for complete search history.

(56) References Cited

U.S. PATENT DOCUMENTS

| | | | |
|---|---|---|---|
| 5,665,398 A | 9/1997 | McCormick | |
| 5,690,892 A | 11/1997 | Babler et al. | |
| 5,968,436 A | 10/1999 | Takezaki | |
| 6,004,512 A | 12/1999 | Titcomb et al. | |
| 6,395,536 B2 | 5/2002 | Freeman | |
| 6,827,907 B2 | 12/2004 | Fattinger et al. | |
| 6,847,481 B1 | 1/2005 | Ludl et al. | |
| 7,407,630 B2 * | 8/2008 | Reed et al. | 422/102 |
| 2001/0003652 A1 * | 6/2001 | Freeman | 435/286.5 |

(Continued)

FOREIGN PATENT DOCUMENTS

DE   27 53 223   7/1981

(Continued)

OTHER PUBLICATIONS

M.J. Schermer; "confocal scanning microscopy . . . "; cited in application; Feb. 28, 2007.

*Primary Examiner*—Jill Warden
*Assistant Examiner*—Jennifer Wecker
(74) *Attorney, Agent, or Firm*—Notaro, Michalos & Zaccaria P.C.

(57) ABSTRACT

A storage unit for biological samples has a horizontal footprint and multiple storage compartments separated by intermediate walls and enclosed by a peripheral frame. The storage compartments have first and second openings and are tailored to the shape of a biopsy cassette or a glass slide and have a retention mechanism preventing the essentially vertical cassettes or slides in the storage compartments through the first opening and/or the second opening from falling out through the first opening and/or the second opening. A transfer system allows at least two storage units or at least one storage unit and one collection unit to be situated one above the other in register and displaced in relation to one another. The transfer system has a manipulator by which a biopsy cassette or a glass slide may be pushed from one storage unit to another, or into the collection unit.

24 Claims, 3 Drawing Sheets

U.S. PATENT DOCUMENTS

| | | | |
|---|---|---|---|
| 2002/0197139 A1* | 12/2002 | Chinbe et al. | 414/416.03 |
| 2004/0251796 A1 | 12/2004 | Wood | |
| 2006/0072988 A1* | 4/2006 | Hariki et al. | 414/282 |
| 2007/0278120 A1* | 12/2007 | Ho Fung et al. | 206/427 |

FOREIGN PATENT DOCUMENTS

| | | |
|---|---|---|
| DE | 43 06 310 | 9/1994 |
| DE | 297 12 535 | 9/1997 |
| EP | 0 904 841 | 9/1998 |
| EP | 0 611 598 | 3/1999 |
| EP | 1 148 372 | 7/2000 |
| GB | 1593 064 | 7/1981 |

* cited by examiner

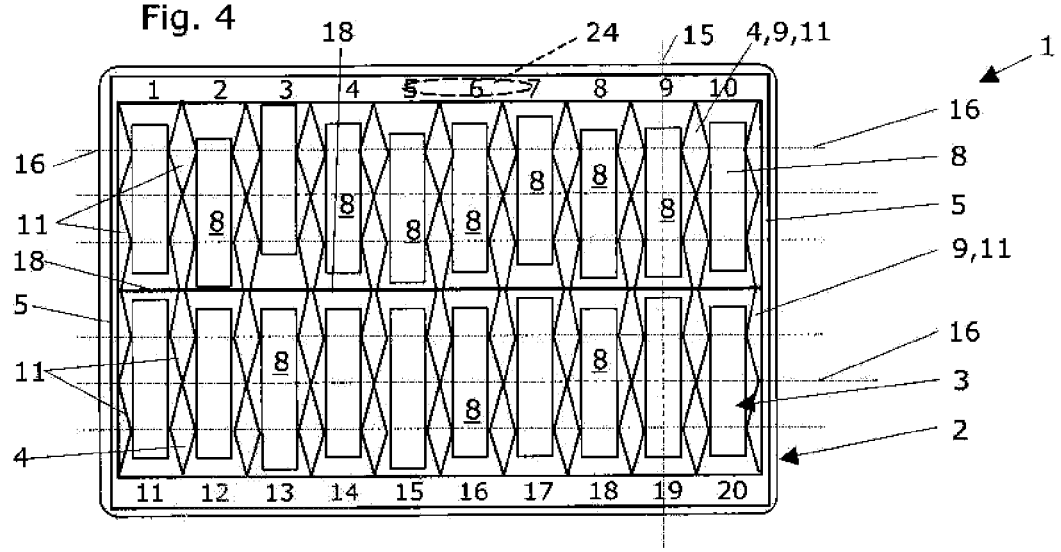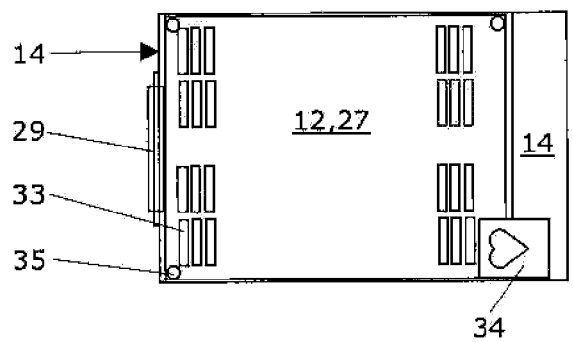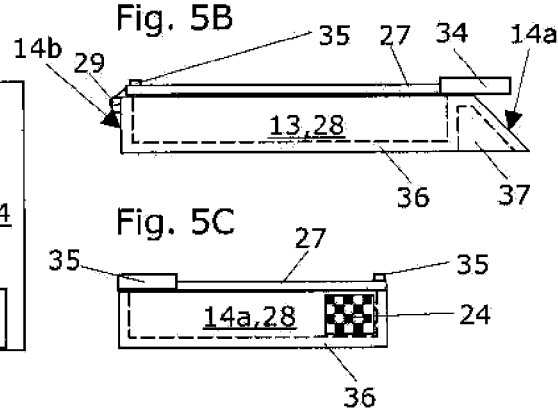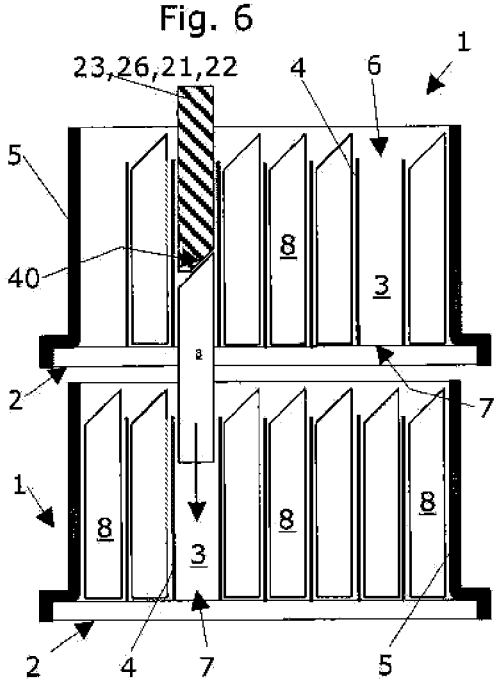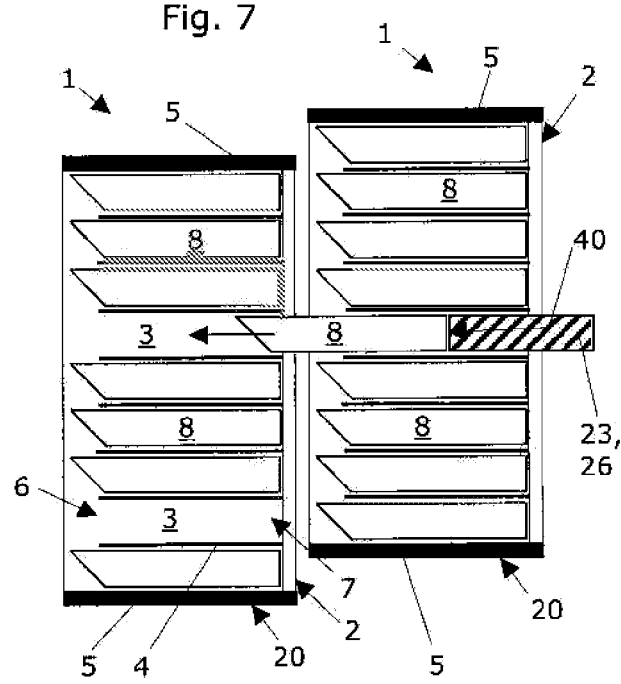

STORAGE UNIT AND TRANSFER SYSTEM FOR STORING AND PROVIDING BIOLOGICAL SAMPLES

RELATED APPLICATIONS

The present patent application claims priority of the Swiss patent Application No. CH 0334/06, filed on Mar. 2, 2006, of which the entire disclosure is herein incorporated by explicit reference for all intents and purposes.

TECHNICAL FIELD OF THE INVENTION

The present invention relates to a storage unit for biological samples having an essentially horizontal main footprint and multiple storage compartments, which are at least partially separated from one another by intermediate walls and are enclosed by a peripheral frame, the intermediate walls and the peripheral frame being situated essentially perpendicularly to the main footprint, and these storage compartments having both a first opening and also a second opening. In addition, the present invention relates to a transfer system which comprises a device, by which at least two such storage units may be situated one on top of another in register and displaced in relation to one another.

Furthermore, the present invention relates to the use of biopsy cassettes or glass slides situated in individual storage compartments of such storage units for biological samples for storing and providing a large number of such biological samples. Each such storage unit comprises an essentially horizontal main footprint and multiple storage compartments, which are at least partially separated from one another by intermediate walls and are enclosed by a peripheral frame. These intermediate walls and the peripheral frame are situated essentially perpendicularly to the main footprint. In addition, these storage compartments have both a first opening and also a second opening.

RELATED PRIOR ART

In biological laboratories, In particular in the laboratories of pathological institutes of universities or hospitals, biological samples, e.g., tissue samples obtained by biopsy, are very often stored as tissue pieces in cassettes or as thin sections on glass slides. A selection of such cassettes and glass slides is offered, for example, by THERMO SHANDON. These cassettes typically comprise a flat, cuboid sample cage having vertical closed lateral walls and a lower support surface pierced in a lattice. The upper storage surface is typically provided by a hinged cover having a snap closure, which is connected via a joint to the sample cage and is also pierced in a lattice. These samples are normally embedded, in paraffin, for example (see, for example, U.S. Pat. No. 5,665,398, U.S. Pat. No. 5,968,436, or DE 43 06 310 A1) and stored at room temperature, in the refrigerator (at approximately +4° C.), in the deep freeze (at approximately −18° C.), at lower temperature in an environment of solid $CO_2$ (at approximately −80° C.), or at extremely low temperature in liquid nitrogen (at approximately −196° C.). A very large number of such samples, which may reach the hundreds of thousands, if not the millions, complicates finding a specific sample. This finding becomes more and more difficult with decreasing storage temperature. The targeted removal of precisely one single sample from a liquid nitrogen container is typically not possible. Normally, a container that contains many samples must be drawn from the nitrogen tank so that the desired sample may be selected. This is a time-consuming process in which the integrity and quality of the other samples which are not selected is also put into play to a greater or lesser degree.

The joint storage of samples typically does not represent a problem for the questions of pathology, contamination of neighboring samples by "carryover" may generally be neglected. A selection of containers for storing and providing such cassettes and glass slides (in particular at room temperature, see also EP 1 148 372 A2) is also offered by THERMO SHANDON. Laboratories of universities and the pharmaceutical industry, who are concerned with protein studies on or in frozen samples, have entirely different requirements in this context.

In pharmaceutical research, chemical or biochemical compounds are routinely tested for their potential pharmaceutical activity. For this purpose, a large number of samples must be provided within a very brief time. In laboratories of pharmaceutical research, microtubes are therefore used, which contain a sufficient quantity of a specific substance. In order to be able to handle the enormous numbers of such microtubes as economically as possible, they are packed in "microtube cluster racks". For robotic handling, those racks, which have a footprint corresponding to the footprint of a microplate according to the SBS standard (SBS=standard for biomolecular screening), which is thus often referred to as the "SBS footprint", are especially preferred. In the meantime, this standard has been normalized by ANSI (American National Standards Institute) as ANSI/SBS 1-2004. Microtube cluster racks having 96 or 384 microtubes are known, for example, under the trade name REMP Tube Technology™.

Thin sections of fixed samples, embedded in paraffin, for example, are routinely applied to glass slides and evaluated using light microscopy in pathology. Following Table 1 gives an overview of the most common glass slides and dimensions:

TABLE 1

| Type | | Inch: 1 × inches | Metric: 25 × 75mm |
| --- | --- | --- | --- |
| Dimensions | Length × width (tolerances) | 76.2 mm × 25.4 mm (±0.5 mm) | 75 mm × 25 mm (±0.5 mm) |
| Thickness | "standard" | 1.02 mm (±0.05 mm) | 1.02 mm (±0.05 mm) |
| Handling | "thick" corners edges surfaces | 1.2 mm (±0.1 mm) sharp, beveled sharp, beveled blank, sandblasted, painted on one or both sides | sharp, rounded sharp blank, sandblasted, painted on one or both sides |

(Table according to: Schermer, M. J.: Confocal scanning microscopy in microarray detection, in "DNA Microarrays, A practical approach"; Mark Schena (ed.), Oxford University Press 1999, 17-42)

The current applicant distributes microtube cluster racks having 96 or 384 microtubes under the trade name REMP Tube Technology™. These differ from the racks and microtubes from the other prior art essentially in that the sample tubes are provided by situating at least two racks one on top of another and sample tubes are pushed from the upper rack using a manipulator into correspondingly positioned receptacle cavities of the lower rack. Vice versa, this transfer process may also be performed by pushing sample tubes using a manipulator from the lower rack into correspondingly positioned receptacle cavities of the upper rack (see, for example, EP 0 904 841 B1 or U.S. Pat. No. 6,827,907 B2).

OBJECT AND SUMMARY OF THE INVENTION

The object of the present invention is to suggest an alternative storage unit—in relation to the one cited at the beginning—for storing and providing a large number of biological samples.

This object is achieved by the features of the claims in that a storage unit for biological samples having an essentially horizontal main footprint and multiple storage compartments is suggested. These storage compartments are at least partially separated from one another by intermediate walls and enclosed by a peripheral frame. The intermediate walls and the peripheral frame are situated essentially perpendicularly to the main footprint. In addition, the storage compartments have both a first opening and also a second opening. The storage unit for biological samples according to the present invention is characterized in that the storage compartments are tailored to the shape of a biopsy cassette or to the shape of a glass slide and comprise retention means, which prevent the biopsy cassettes or glass slides, which are inserted through the first opening and/or the second opening into the storage compartments and stand essentially vertically, from falling out through the first opening and/or the second opening. Additional preferred and inventive features result from the dependent claims.

Advantages of the storage unit for biological samples according to the present invention comprise:

- The biopsy cassettes or glass slides having the biological samples may be inserted into the storage compartments robotically.
- The biopsy cassettes or glass slides having the biological samples may be removed from the storage compartments robotically.
- The biopsy cassettes or glass slides having the biological samples may be repositioned from one storage compartment to another storage compartment of the same storage unit robotically.
- The biopsy cassettes or glass slides having the biological samples may be repositioned from one storage compartment to another storage compartment of another storage unit robotically.
- Each biopsy cassette and each glass slide having the biological samples contained therein or thereon may be addressed individually and stored and provided robotically without any influence on other samples.
- The robotic storage and provision of the biopsy cassettes and glass slides having the biological samples contained therein or thereon may be performed at practically any arbitrary temperature.

BRIEF INTRODUCTION OF THE DRAWINGS

Exemplary embodiments of the storage unit according to the present invention will now be explained in greater detail on the basis of schematic figures of the drawing, which do not restrict the scope of the present invention, wherein:

FIG. 4 shows a second top view of a storage unit suitable for biopsy cassettes, in which the essentially vertically standing biopsy cassettes are packed loosely and situated transversely;

FIG. 5 shows views of a closed biopsy cassette known per se from the prior art, wherein FIG. 5A shows a top view of the support surface of the cover of the biopsy cassette;

FIG. 5B shows a view of a vertical surface of the cage of the biopsy cassette; and FIG. 5C shows a view of the forward face of the cage of the biopsy cassette;

FIG. 6 shows a vertical section through two storage units situated one above the other in register having the SPS standard footprint of a standard microplate, a biopsy cassette being pushed vertically from the upper storage unit into the lower storage unit;

FIG. 7 shows a vertical section through two storage units situated one above the other in register, a biopsy cassette being pushed horizontally from the lower storage unit into the upper storage unit;

DETAILED DESCRIPTION OF THE INVENTION

Figure 1:
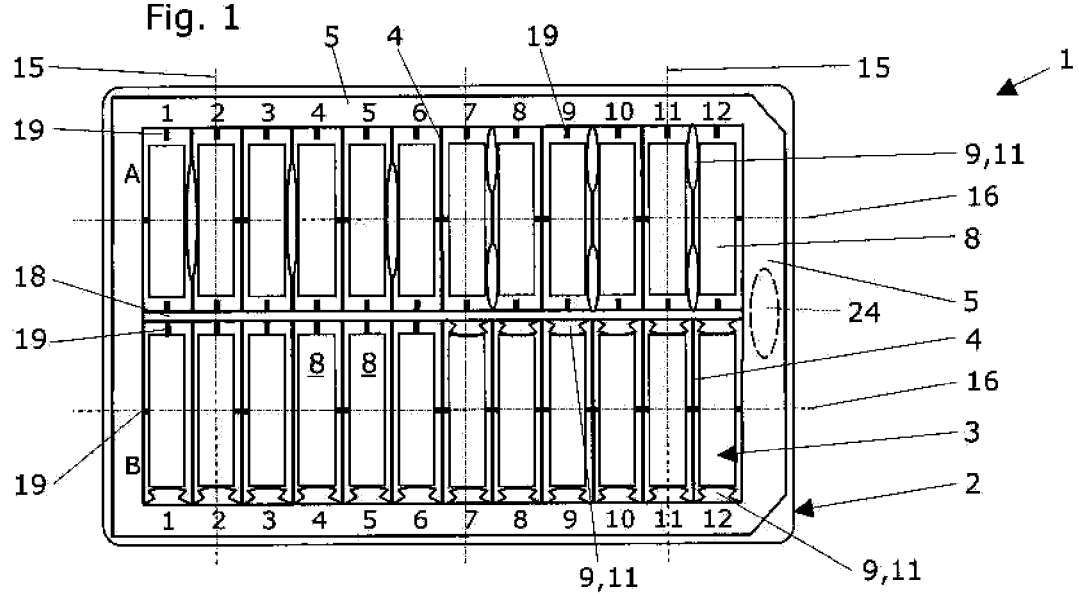
FIG. 1 shows a top view of a storage unit suitable for biopsy cassettes, in which the essentially vertically standing biopsy cassettes are packed tightly and situated transversely.

FIG. 1 shows a storage unit 1 for biological samples, having a main footprint 2 and multiple storage compartments 3, which are at least partially separated from one another by intermediate walls 4 and are enclosed by a peripheral frame 5, the intermediate walls 4 and the peripheral frame 5 being situated essentially perpendicularly to the main footprint 2, and its storage compartments 3 having a first opening 6 and also a second opening 7 (see FIGS. 6 and 7). The storage compartments 3 have the same, essentially rectangular cross-sectional profile over their entire height in the storage unit 1 here. The storage compartments 3 are tailored to the shape of a biopsy cassette 8, which is inserted either through the first opening 6 or the second opening 7 into these storage compartments 3 standing essentially vertical and stands on one of its faces 14 (see FIG. 5C). The storage compartments 3 additionally comprise retention means 9, which are implemented here as single-sided and double-sided cushions 11. The retention means 9 run essentially perpendicularly in relation to the main footprint 2 and are implemented to engage using friction lock on the support surfaces 12 (see FIG. 5A) or on the vertical surfaces 13 (see FIG. 5B) of a biopsy cassette 8 inserted into a storage compartment 3. Due to this friction lock, these essentially vertically inserted biopsy cassettes 8 are prevented from falling out through the first opening 6 and/or the second opening 7 (no matter which side the storage unit 1 is tilted toward).

According to a first embodiment, the cushions 11 are implemented as double-sided, as shown in the storage compartments A1 through A12. In connection with the present invention, "double-sided" is to be understood to mean "acting in two directions against the biopsy cassettes which press against them". These cushions 11 are implemented to engage using friction lock on the support surfaces 12 of a biopsy cassette 8 inserted into a storage compartment 3 and are situated on a longitudinal axis 16 (see storage compartments A1 through A6) running centrally and transversely to these storage compartments 3. The double-sided cushions 11 of a row of storage compartments (see A7 through A12) are situated on two longitudinal axes 16 running transversely to these storage compartments 3. To improve the stability of the storage unit 1, it preferably has a middle wall 18. The biopsy cassettes 8 to be inserted are provided with an additional guide by guide lamellae 19. These guide lamellae 19 preferably run perpendicularly to the main footprint 2 and may alternately be situated on the middle wall 18, on the intermediate walls 4, and on the peripheral frame 5. These guide lamellae 19 preferably project perpendicularly from their supporting wall into the storage compartments 3; those guide lamellae 19 which taper toward the first and second openings 6, 7 and thus form an intake for the biopsy cassettes 8 to be inserted are especially preferred (not shown).

According to a second embodiment, the cushions 11 are implemented as single-sided, as shown in the storage compartments B1 through B12. In connection with the present invention, "single-sided" is to be understood to mean as "acting in one direction against the biopsy cassette which presses against them". These cushions 11 are implemented to engage using friction lock on the vertical surfaces 13 of a biopsy cassette 8 inserted Into a storage compartment 3 and are situated on a transverse axis 15 running centrally and longitudinally to this storage compartment 3.

As already shown on the basis of FIG. 1, the elements of cushions 11 and guide lamellae 19 may be selected and/or combined with one another practically arbitrarily. The main footprint 2 of such a storage unit 1 preferably corresponds at least approximately to the SBS standard footprint of a standard microplate.

With the goal of a housing as many biopsy cassettes 8 as possible in the storage unit 1 shown in FIG. 1, two rows having 12 storage compartments 3 each are situated standing essentially vertically in such a way that the biopsy cassettes 8, which stand on their faces 14 in relation to the main footprint 2, are situated transversely to the longitudinal direction of the storage unit 1. This results in a total of 24 cassettes 8 per storage unit 1 at the selected axial spacing of approximately 9 mm. If the peripheral frame 5 was narrowed, two additional cassettes could be housed in this storage unit 1; however, the position indicators would be significantly smaller or would have to be left out entirely.

As shown, the storage unit 1 has two beveled corners as orientation aids. These orientation aids may be partially or entirely dispensed with. Alternative orientation aids may be provided, for example, by a rounded corner or also by a corner equipped with a notch or a special relief (not shown). Attaching a bar code to an external surface of the peripheral frame and/or attaching a radiofrequency label, i.e., an "RFID tag", offers a further possibility. RFID tags, which not only have an individual, stored and retrievable identification code, but additionally comprise a writable and retrievable additional data memory are especially preferred. Attaching these RFID tags to locations on or in the storage unit 1 at which no mechanical action on these RFID tags is a concern is preferable. Barcodes are used alternatively or additionally to the RFID tags and are preferably provided in one-dimensional or two-dimensional form.

Figure 2:
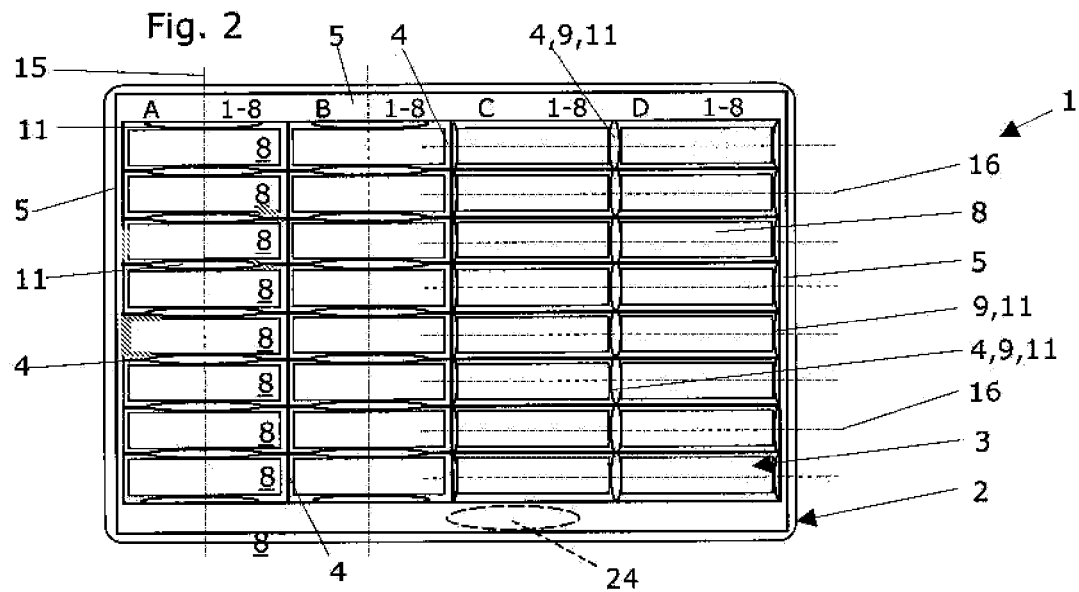
FIG. 2 shows a top view of a storage unit suitable for biopsy cassettes, in which the essentially vertically standing biopsy cassettes are packed tightly and situated longitudinally.

FIG. 2 shows a top view of a storage unit 1 for biological samples suitable for biopsy cassettes, in which the essentially vertically standing biopsy cassettes 8 are tightly packed and are situated longitudinally in relation to the longitudinal orientation of the storage unit 1. This storage unit 1 also comprises a main footprint 2 and multiple storage compartments 3, which are at least partially separated from one another by intermediate walls 4 and are enclosed by a peripheral frame 5. The intermediate walls 4 and the peripheral frame 5 are situated essentially perpendicularly to the main footprint 2. In addition, these storage compartments 3 have both a first opening 6 and also a second opening 7 (see FIGS. 6 and 7). The storage compartments 3 have the same, essentially rectangular cross-sectional profile over their entire height in the storage unit 1. The storage compartments 3 are tailored to the shape of a biopsy cassette 8, which is inserted either through the first opening 6 or the second opening 7 into these storage compartments 3 and stands on one of its faces 14 (see FIG. 5C). The storage compartments 3 additionally comprise retention means 9, which are implemented here as single-sided and double-sided cushions 11. The retention means 9 run essentially perpendicularly to the main footprint 2 and are implemented to engage using friction lock on the support surfaces 12 (see FIG. 5A) or on the vertical surfaces 13 (see FIG. 5B) of a biopsy cassette 8 inserted into a storage compartment 3. These inserted biopsy cassettes 8 are prevented from falling out through the first opening 6 and/or the second opening 7 by this friction lock (no matter which side the storage unit 1 is tilted toward). The cushions 11 are also implemented as single-sided or double-sided here.

In the storage compartments A1, A8, B3 and B8, the cushions 11 are situated on the peripheral frame 5 and implemented to act single-sided. In the storage compartments A2 through A7 and B2 through B7, the cushions 11 are situated on the intermediate walls 4 and implemented to act double-sided. In the storage compartments C1 through C8 and D1 through D8, the cushions 11 are situated on the peripheral frame 5 or on the intermediate walls 4 and are implemented to act single-sided or double-sided accordingly. All of these cushions 11 are implemented to engage using friction lock on the support surfaces 12 or on the vertical surfaces 13 of a biopsy cassette 8 inserted into a storage compartment 3. Half of these (see storage compartments A1 through A8 and B1 through B8) are situated on a transverse axis 15 running centrally and transversely to these storage compartments 3. The other half (see storage compartments C1 through C8 and D1 through D8) is situated on a longitudinal axis 16 running centrally and longitudinally to these storage compartments 3.

As shown, all or a part of the middle walls may be formed by the cushions 11. In order to improve the stability of the storage unit 1, it may have a reinforced middle wall 18 (not shown). Because of the tight space conditions existing here, which cause very precise positioning of the biopsy cassettes 8, guide lamellae 19 are dispensed with here. With the goal of housing as many biopsy cassettes 8 as possible in the storage unit 1 shown in FIG. 2, four rows having eight storage compartments 3 each are situated in such a way that the biopsy cassettes 8, which stand on their faces 14 in relation to the main footprint 2, are situated longitudinally to the longitudinal direction of the storage unit 1. This results in a total of 32 cassettes 8 per storage unit 1 at the selected axial spacing of approximately 9 mm. If the peripheral frame 5 was narrowed, four additional cassettes could be housed in this storage unit 1; however, the position indicators would then be significantly smaller or would have to be left out entirely.

Figure 3:
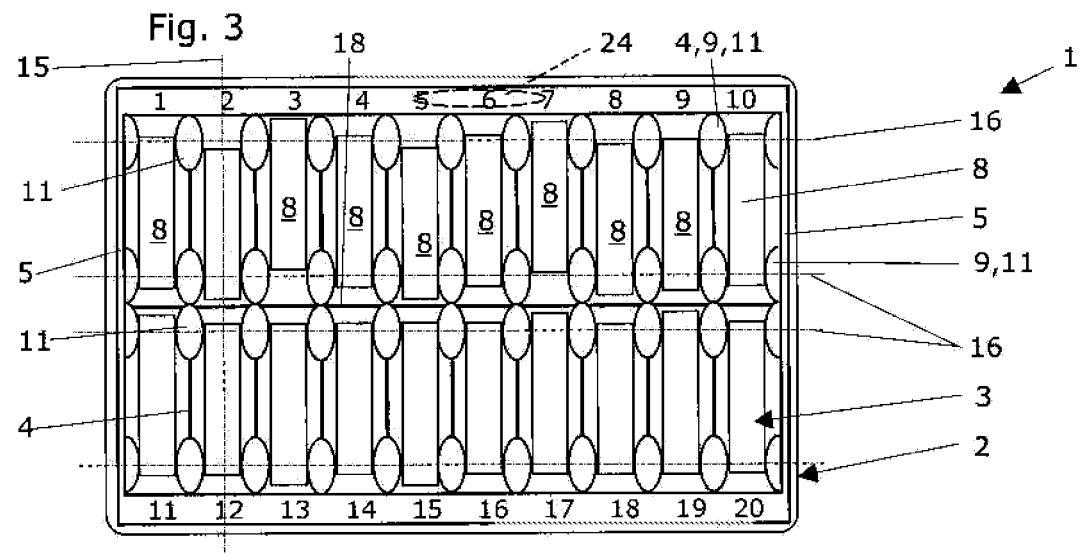
FIG. 3 shows a first top view of a storage unit suitable for biopsy cassettes, in which the essentially vertically standing biopsy cassettes are packed loosely and situated transversely.

FIG. 3 shows a first top view of a storage unit 1 suitable for biopsy cassettes, in which the essentially vertically standing biopsy cassettes 8 are loosely packed and situated transversely. In contrast to the two storage units 1 described above, the number of the insertable biopsy cassettes 8 is reduced to a total of twenty and cushions 11 having a larger volume are used. In addition, guide lamellae 19 were dispensed with. The storage unit 1 also comprises a main footprint 2 and multiple storage compartments 3 here, which are at least partially separated from one another by intermediate walls 4 and are enclosed by a peripheral frame 5. The intermediate walls 4 and the peripheral frame 5 are also situated essentially perpendicularly to the main footprint 2. In addition, the storage compartments 3 have both a first opening 6 and also a second opening 7 (see FIGS. 6 and 7). The storage compartments 3 have the same, essentially rectangular cross-sectional profile over their entire height in the storage unit 1 here, The storage compartments 3 are tailored to the shape of a biopsy cassette 8, which has been inserted either through the first opening 6 or the second opening 7 into these storage compartments 3 and stands on one of its faces 14 (see FIG. 5C).

The purpose of this embodiment is to provide those storage compartments 3, which leave greater play for the dimensions of the biopsy cassettes 8 to be inserted. In addition, this embodiment of the storage unit 1 allows quite imprecise insertion of the biopsy cassettes 8, but nonetheless ensures these biopsy cassettes 8 are held securely in the storage compartments 3. In order to improve the stability of the storage unit 1, it may have a reinforced middle wall 18 (not shown).

The single-sided acting cushions 11 are situated on the peripheral frame 5 in the storage compartments 1, 10, 11, and 20, All double-sided acting cushions 11 are situated in the area of the intermediate walls. All of these cushions 11 are implemented to engage using friction lock on the support surfaces 12 of a biopsy cassette 8 inserted into a storage compartment 3 and are situated in a row of storage compartments (see 1 through 10 and 11 through 20) on two longitudinal axes 16 running transversely to these storage compartments 3, FIG. 4 shows a second top view of a storage unit 1 suitable for biopsy cassettes, in which the essentially vertically standing biopsy cassettes 8 are loosely packed and situated transversely. In contrast to FIG. 3, the cushions 11 are implemented as rhomboidal in cross-section and not elliptical In addition, the most pronounced points of the cushions are placed so that they are at a distance of approximately a fourth of the length of a storage compartment 3 from the peripheral frame 5 or the middle wall 18. This configuration in turn allows storage compartments 3 to be provided which allow greater play for the dimensions of the biopsy cassettes 8 to be inserted. In addition, this embodiment of the storage unit 1 also allows quite imprecise insertion of the biopsy cassettes 8, but nonetheless ensures that these biopsy cassettes 8 are held securely in the storage compartments 3. In order to improve the stability of the storage unit 1, it may have a reinforced middle wall 18 (not shown). The intermediate walls 4 are replaced entirely by the cushions 11 here, which provide a larger spring path for the cushions.

Because the embodiments of the storage compartments 3 shown in FIG. 3 and FIG. 4 include a larger space around the inserted biopsy cassettes 8, storage units 1 of this type are especially well suitable for storing the biopsy cassettes 8 at low (−80° C.) or very low temperatures (−196° C.). This larger space improves the gas exchange in the immediate surroundings of a cassette, so that it is well reachable and optimally cooled by the $CO_2$ cooling gas or the liquid nitrogen. The single-sided or double-sided cushions 11 preferably extend at the same effective cross-section over essentially the entire height of the storage compartments 3 and are preferably implemented as open in the area of the first opening 6 and the second opening 7. These cushions may additionally have passages or be implemented as net-like (not shown).

FIG. 5 shows views of a closed biopsy cassette, known per se from the prior art, made of injection-molded plastic, such as polypropylene. The interior of such a cassette typically measures approximately 30×25×5 mm, FIG. 5A shows a top view of the support surface 12 of the cover 27 of the biopsy cassette 8. The cover 27 has multiple slots 33, of which only a part are shown. The cover 27 is connected via the hinge 29 to the cage 28, of which the beveled face 14a is well visible on the right side. A tab 34 shaped onto the cover makes it easier to open the cassette by hand. In the corners of the biopsy cassette 8 not occupied by the tab, pins 35 are located, which define a shared level together with the tab 34.

FIG. 5B shows a view of a vertical surface 13 of the cage 28 of the biopsy cassette 8. The hinge 29 and a pin 35 are shown on the left side. The tab 34 and the beveled front face 14a are indicated on the right side. The curve of the floor 36 of the cassette 8 is drawn using dashed lines.

FIG. 5C shows a view of the beveled front face 14a of the cage 28 of the biopsy cassette 8. The tab 34 and a pin 35 are visible in the area of the cover 27. A two-dimensional bar code is printed on the right side. The course of the floor 36, which comprises a similar slotted pattern as the cover 27 of the cassette (not shown), is drawn using dashed lines.

FIG. 6 shows a vertical section through two storage units 1 situated one above the other in register, having a main footprint 2 corresponding to the SBS standard footprint of a standard microplate, a biopsy cassette 8 being pushed at least essentially vertically by a manipulator 23 from the upper storage unit into the lower storage unit (toward the main footprint 2) precisely at this instant. The manipulator 23 is part of the device 22 of a transfer system 21, using which at least two storage units 1 may be situated one above the other in register and displaced in relation to one another. The storage units 1 shown are located in a mutual position, in which all storage compartments 3 corresponding to one another of these two storage units 1 are placed precisely one above another. At least one of these two storage units 1 may be displaced in relation to the other using the device 22 in such a way that any arbitrary storage compartment 3 of the upper storage unit 1 may be assigned to an arbitrary storage compartment 3 of the lower storage unit 1 standing exactly in register in relation to one another. It is then easy to insert a preferably robotic manipulator 23 into a specific and individually selected storage compartment 3 and push the biopsy cassette 8 located therein into a previously assigned storage compartment 3 of a second storage unit 1 (toward the main footprint 2). The sliding resistance caused by the friction lock between the retention means 9 and the biopsy cassette 8 to be displaced causes this biopsy cassette not to fall out after it is transferred from the upper storage unit 1 into the lower storage unit 1. The manipulator 23 is preferably tailored to the shape of the front, beveled face 14a of the biopsy cassette 8 and may have a friction-increasing coating, which prevents slipping on the beveled face 14a of the biopsy cassette 8.

As shown, the biopsy cassette 8 are preferably inserted essentially vertically into the storage compartments 3 of a storage unit 1 in such a way that the front, beveled faces 14a of the biopsy cassettes 8 are on top and may be read from this direction by eye or automatically using an appropriate reading device. An RFID tag is preferably housed in the dead-end space 37 on the bottom of the biopsy cassette 8 (see FIG. 5B).

Alternatively to the pushing direction shown of the manipulator 23, it may also run in the opposite direction, i.e., from bottom to top (not shown). Notwithstanding the illustration in FIG. 6, the bottom storage unit may have a closed floor (not shown) and solely be used as a collection unit for biopsy cassettes 8. Therefore, the use of at least one storage unit 1 for biopsy cassettes 8 suffices to perform the alternative method, in which selected biopsy cassettes 8 are transferred from one storage unit 1 or multiple such storage units to a collection unit for biopsy cassettes 8.

FIG. 7 shows a vertical section through two storage units 1 situated one above the other in register having a main footprint 2 deviating from the SBS standard footprint of a standard microplate, a biopsy cassette 8 being pushed at least essentially horizontally by a manipulator 23 from the lower storage unit into the upper storage unit (away from the main footprint 2) precisely at this instant. The two storage units 1 stand on a secondary footprint 20, which is oriented essentially perpendicularly to the main footprint 2. Notwithstanding the illustration selected here, these two storage units 1 may have a secondary footprint 20 and a main footprint 2 corresponding to the SBS standard footprint of a standard microplate.

The manipulator 23 is part of the device 22 of a transfer system 21, using which at least two storage units 1 are situated one above the other in register and may be displaced in relation to one another. The storage units 1 shown are located in a mutual position, in which only a part and storage compartments 3 not corresponding to one another of these two storage units 1 are placed precisely one above the other. At least one of these two storage units 1 was displaced in relation to the other using the device 22 in such a way that any arbitrary storage compartment 3 of the upper storage unit 1 is assigned to an arbitrary storage compartment 3 of the lower storage unit 1 standing exactly in register one over the other, A preferably robotic manipulator 23 is inserted into a specific and individually selected storage compartment 3 and the biopsy cassette 8 located therein is pushed into a previously assigned storage compartment 3 of the other storage unit 1 (away from the main footprint 2). The sliding resistance caused by the friction lock between the retention means 9 and the biopsy cassette 8 to be displaced causes this biopsy cassette not to fall out after it is transferred from the lower storage unit 1 into the upper storage unit 1. The manipulator 23 is preferably tailored to the shape of the rear, non-beveled face 14b of the biopsy cassette 8 and may have a friction-increasing coating, which prevents slipping on this face 14b of the biopsy cassette 8.

As shown, the biopsy cassettes 8 are preferably inserted here into the storage compartments 3 of a storage unit 1 in such a way that the front, beveled faces 14a of the biopsy cassettes 8 are in front (away from the main footprint 2) and may be read from this direction by eye or automatically using a corresponding read device. An RFID tag is preferably housed in the dead-end space 37 on the bottom of the biopsy cassette 8 (see FIG. 5B).

Alternatively to the pushing direction shown of the manipulator 23, it may also run in the opposite direction, i.e., from front to rear (i.e., from left to right, not shown). Notwithstanding the illustration in FIG. 7, the upper storage unit may have a closed floor (not shown) and solely be used as a collection unit for biopsy cassettes 8.

Figure 8:
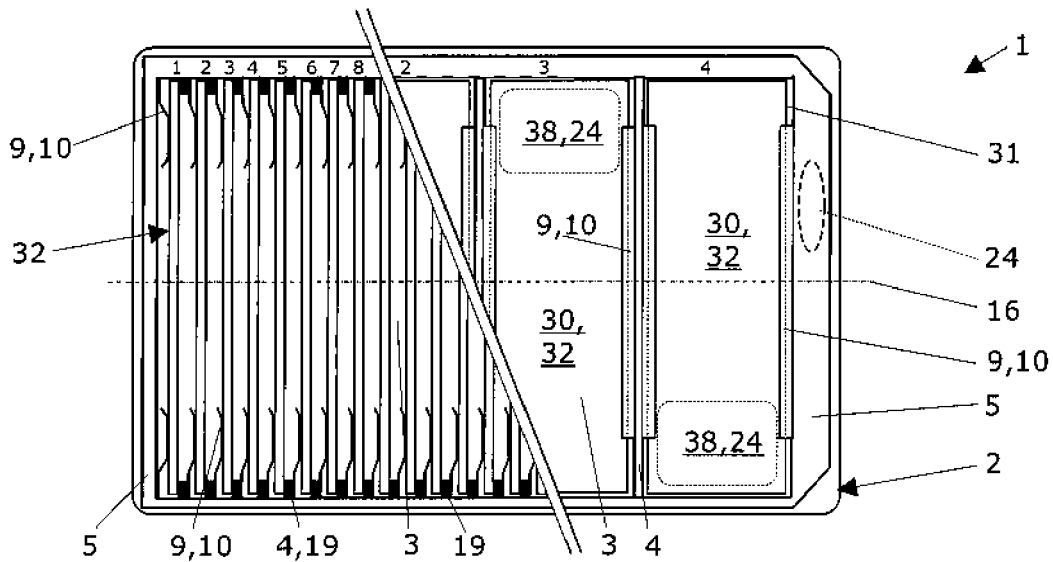
FIG. 8 shows a top view of a storage unit suitable for glass slides, in which the glass slides are situated transversely and standing essentially vertically, tightly packed or transversely and lying.

FIG. 8 shows a top view of a storage unit 1 suitable for glass slides, in which the glass slides 30 are tightly packed transversely and standing essentially vertically (left side FIG. 8) or transversely and lying (right side FIG. 8). In these configurations, it is unimportant in principle how the surface of the object carrier, to which the samples, i.e., for example, the tissue sections (e.g., from pathology), cell smears (e.g., blood smears), or cell layers (e.g., from a cell culture) are located, stands or lies. In any case, it is ensured that the sample regions of the glass slides 30 are not mechanically strained.

This storage unit 1 for biological samples has an essentially horizontal main footprint 2 and multiple storage compartments 3, which are at least partially separated from one another by intermediate walls 4 and are enclosed by a peripheral frame 5. The intermediate walls 4 and the peripheral frame 5 are situated essentially perpendicularly to the main footprint 2. In addition, these storage compartments 3 have both a first opening 6 and also a second opening 7. The storage compartments 3 are tailored to the shape of a glass slide 30 and comprise retention means 9 which prevent the glass slides 30 inserted through the first opening 6 and/or the second opening 7 into the storage compartments 3 from falling out through the first opening 6 and/or the second opening 7. The storage compartments 3 preferably have an essentially rectangular cross-section and are implemented to each receive one glass slide 30 for biological samples either standing on a longitudinal edge 31 or lying on a surface 32 in relation to the main footprint 2.

The retention means 9 are preferably selected from a group which comprises single-sided and double-sided lamellae 10. In connection with the present invention, "single-sided" is to be understood to mean "acting against a slide which presses against it". In connection with the present invention, "double-sided" is to be understood to mean "acting against two slides which press against it". The retention means 9 (lamellae 10 here) run either essentially perpendicularly to the main footprint 2 (see left side of FIG. 8) or essentially parallel to the main footprint 2 (see right side of FIG. 8).

The lamellae 10 situated essentially perpendicularly to the main footprint 2 are implemented to engage using friction lock on the surface 32 of a glass slide 30 inserted essentially vertically into a storage compartment 3. This inserted glass slide 30 is prevented from falling out through the first opening 6 and/or the second opening 7 (no matter which side the storage unit 1 is tilted toward) by this friction lock. These lamellae 10 begin at the peripheral frame 5 (not shown) or at its guide lamellae 19 which extend perpendicularly to: the main footprint 2. These guide lamellae 19 assume the function of the intermediate walls 4 and thus at least partially separate the storage compartments 3 from one another. The lamellae 10 are preferably implemented as only wide enough that they do not reach the sample areas of the glass slides 30. The lamellae 10 impinge the glass slides 30 and press them elastically against the guide lamellae 19, 50 that the glass slides 30 are held securely in their storage compartments 3. The dense packing of the storage compartments 3 allows up to 24 or more glass slides 30, which preferably stand essentially vertically on a longitudinal edge 31, to be situated in a single storage unit 14.

The lamellae 10 situated essentially parallel to the main footprint 2 are implemented to rest partially on the surface 32 of a glass slide 30 inserted into the storage compartment 3. These inserted glass slides 30 are prevented from falling out through the first opening 6 and/or the second opening 7 (no matter which side the storage unit 1 is tilted toward) by this partial contact. The lamellae 10 are shaped onto the top and bottom of the intermediate walls 4 here or attached thereto (e.g., by welding or gluing, not shown) and project on both sides beyond these intermediate walls 4 (see FIG. 10). The upper and lower lamellae 10 situated on the peripheral frame 5 are preferably at the same height as the corresponding lamellae attached to the intermediate walls 4. However, the lame lamellae 10 are preferably implemented as only wide enough that they do not reach the sample areas of the glass slide 30. The lamellae 10 may be implemented in one piece and extend over a partial length of the storage compartment 3 (see FIG. 8, right side); however, they may also be divided (not shown). In an alternative configuration of the lamellae 10, they are situated on the transverse sides of the storage compartments 3 (not shown). Combinations of the configurations shown and alternative configurations are also provided. The horizontal configuration allows the storage of up to 4 glass slides 30 in a storage unit 1.

Figure 9:
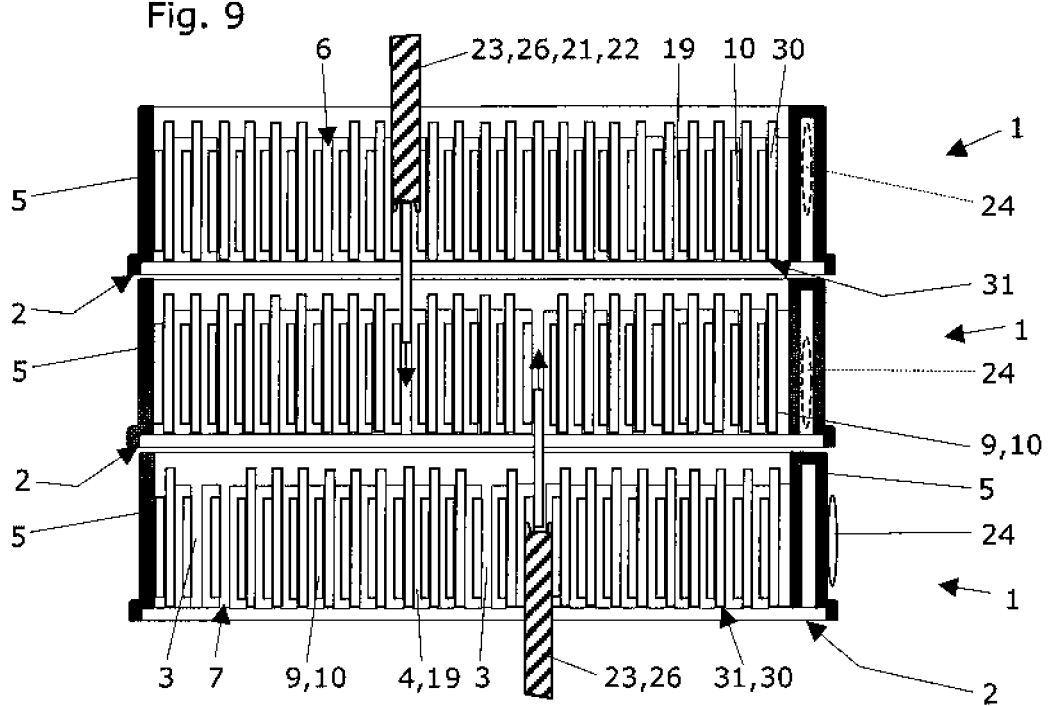
FIG. 9 shows a vertical section through three storage units situated one above the other in register having the SPS standard footprint of a standard microplate, a standing glass slide being pushed vertically from the upper storage unit into the middle storage unit and from the lower storage unit into the middle storage unit.

FIG. 9 shows a vertical section through three storage units 1 situated one on top of another in register having a main footprint 2 corresponding to the SPS standard footprint of a standard microplate. Precisely one essentially vertically standing glass slide 30 is pushed by a first manipulator 23 vertically from the upper storage unit into the middle storage unit (toward the main footprint 2) and one glass slide is pushed by a second manipulator 23 from the lower storage unit into the middle storage unit (away from the main footprint 2) precisely at this instant.

The manipulator 23 is part of the device 22 of a transfer system 21, using which at least two storage units 1 may be situated one above the other in register and displaced in relation to one another. The storage units 1 shown are located in a mutual position in which all storage compartments 3 of these two storage units 1 corresponding to one another are placed precisely one above another. At least one of these two storage units 1 may be displaced in relation to the other using the device 22 in such a way that any arbitrary storage compartment 3 of the upper storage unit 1 may be assigned standing in register directly in relation to another an arbitrary storage compartment 3 of the lower storage unit 1. It is then easy to insert a preferably robotic manipulator 23 into a specific and individually selected storage compartment 3 and to push the glass slide 30 located therein into a previously assigned storage compartment 3 of a second storage unit 1 (e.g., toward the main footprint 2). The sliding resistance caused by the friction lock between the retention means 9 and the glass slide 30 causes this glass slide 30 not to fall out after it is transferred from the upper storage unit 1 into the lower storage unit 1. The manipulator 23 is preferably tailored to the shape of the essentially vertically standing glass slide 30 and may additionally have a friction-reinforcing coating, which prevents slipping on the longitudinal edge 31 of the glass slide 30.

As shown in FIG. 9, the glass slides 30 are preferably inserted standing essentially vertically on a longitudinal edge 31 into the storage compartments 3 of a storage unit 1 in such a way that they have a distance (if minimal) from one another. Identifiers 24 (e.g., in the form of barcode markings) are preferably attached along the upper longitudinal edge 31 and/or in the area proximal to these longitudinal edges of grip areas 38 situated on the narrow sides (see also FIG. 8), so that these may be read by eye or automatically using a corresponding read device. An RFID tag 39 is preferably attached in a grip area 38 of the glass slide 30 (see FIG. 8).

Alternatively to the first pushing direction of the manipulator 23, it may also run in the opposite direction, i.e., from bottom to top. Notwithstanding the illustration in FIG. 9, only one storage unit 1 and a collection unit may also be used, the collection unit being able to lie on the top or bottom, having a closed floor (not shown) on the side distal from the storage unit 1, and solely being used as a collection unit for glass slides 30. Therefore, the use of at least one storage unit 1 for glass slides 30 suffices to perform the alternative method, in which selected glass slides 30 are transferred from one storage unit 1 or multiple such storage units to a collection unit for glass slides 30.

Notwithstanding FIG. 9 and corresponding to the configurations shown in FIG. 7, two storage units 1 situated one above the other in register may additionally or alternatively be equipped with a main footprint 2 deviating from the SPS standard footprint of a standard microplate. These alternative storage units 1 stand on this secondary footprint 20, which is oriented essentially perpendicularly to the main footprint 2. A preferably robotic manipulator 23 is inserted into a specific and individually selected storage compartment 3 and pushes the glass slide 30 located therein into a previously assigned storage compartment 3 of the other storage unit 1 (away from the main footprint 2). The sliding resistance caused by the friction lock between the retention means 9 and the glass slide 30 to be displaced causes this glass slide 30 not to fall out of this storage unit 1 after it is transferred. Alternatively to the indicated pushing direction of the manipulator 23, it may also run in the opposite direction, i.e., from left to right (not shown). The upper storage unit may also have a closed floor or cover (not shown) and solely be used as a collection unit for glass slides 30.

Figure 10:
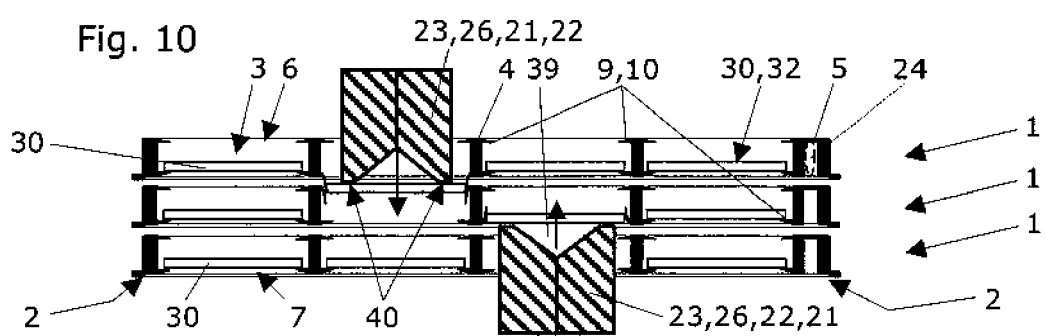
FIG. 10 shows a vertical section through three storage units situated one above the other in register having the SPS standard footprint of a standard microplate, a lying glass slide being pushed vertically from the upper storage unit into the middle storage unit and from the lower storage unit into the middle storage unit.

FIG. 10 shows a vertical section through three storage units 1, situated one above another in register, having a main footprint 2 corresponding to the SPS standard footprint of a standard microplate. At this instant, one essentially horizontally lying glass slide 30 is pushed by a first manipulator 23 vertically from the upper storage unit 1 into the middle storage unit (toward the main footprint 2) and one glass slide is pushed by a second manipulator 23 from the lower storage unit 1 vertically into the middle storage unit (away from the main footprint 2). During the transfer pushing of the essentially horizontally lying slide 30, it is pressed against the closest lamellae 10 of the storage unit 1, in which the slide 30 initially lies. These lamellae 10 may be those, which constrict the first opening 6 of the original storage compartment 3. These lamellae 10 may, however, also be those on which the slide 30 rests and which constrict the second opening 7 of the original storage compartment 3. During the further movement of the slide 30, these lamellae are elastically deformed by the slide 30, so that the lamellae 10 yield elastically with deformation and temporarily impinge the two longitudinal edges (see FIG. 9) with a friction lock, for example. The slide 30 is pushed further by the manipulator 23 against this sliding resistance, the lamellae 10 delimiting the storage compartment 3 of the next storage unit 1 also elastically yielding and temporarily impinging the slide 30 with a friction lock. If the slide 30 is conveyed from top to bottom, it falls on the supporting lamellae 10 of the new storage unit 1 as soon as it has left the influence range of the lamellae just deformed. If the slide 30 is conveyed from bottom to top, it is moved further nearly up to the lamellae 10 constricting the new storage compartment 3 on top. The slide 30 thus leaves the influence range of the lamellae just deformed, which immediately spring back into their essentially vertical original position. The manipulator 23 may now be lowered and the slide 30 conveyed from bottom to top remains lying on the lamellae 10 of the new storage unit 1 which support it.

It results from this description that the transferred slide 30 is moved over at least a part of its transfer path from one storage unit 1 to the other against the sliding resistance of lamellae 10. This sliding resistance allows careful depositing of a slide 30 pushed from top to bottom in particular. The manipulator 23 has recesses 39, thanks to which the samples on the slide 30 are not strained. The manipulator 23 may have a coating on its pushing faces 40 to increase the sliding resistance of the slide 30 and/or to softly and elastically impinge the slide 30.

A preferred transfer system for transferring biopsy cassettes 8 or slides 30 from one storage unit 1 to a second storage unit 1 or to a collection unit preferably comprises a device 22, using which at least two storage units 1 or at least one storage unit 1 and one collection unit may be situated one above the other in register and displaced in relation to one another. Such a transfer system 21 preferably additionally comprises a manipulator 23, using which a biopsy cassette 8 inserted into an individual storage compartment 3 or a glass slide 30 inserted into an individual storage compartment 3 may be pushed from one storage unit 1 into the other storage unit 1 or into the collection unit.

In a first preferred transfer system, the device 22 is implemented for situating the at least two storage units 1 or at least one storage unit 1 and one collection unit in essentially horizontal planes which lie one above the other. In addition, the manipulator 23 is implemented for essentially vertically pushing a biopsy cassette 8 or a glass slide 30 toward the main footprint 2 or away therefrom.

In a second preferred transfer system 21, the device 22 is implemented for situating the at least two storage units 1 or at least one storage unit 1 and one collection unit in essentially vertical planes which lie one above the other and this manipulator 23 is implemented for essentially horizontally pushing a biopsy cassettes 8 or a glass slide 30 toward the main footprint 2 or away therefrom.

Such transfer systems 21 preferably additionally comprise a warehouse unit 25 for storing multiple storage units 1 according to one of claims 1 through 15 and a robot 26, using which such storage units 1 may be removed from the warehouse unit 25 and/or stored in this warehouse unit 25. Warehouse units 25 which comprise an array of retainers 27 having bearing surfaces 17 are especially preferred, the bearing surfaces 17 of these retainers 27 being implemented to be impinged by the main footprint 2 or a secondary footprint 20 of a storage unit 1.

The storage units 1 according to the present invention and the biopsy cassettes 8 or glass slides 30 comprise at least one identifier 24, which is selected from RFID tags and barcodes, for unique identification and tracking, The storage units 1 according to the present invention are preferably produced in the injection molding method and comprise a polymer or multiple polymers, which preferably include polycarbonate (PC).

The use of biopsy cassettes 8 or glass slides 30 situated in individual storage compartments 3 of storage units 1 according to the present invention for biological samples has the purpose of storing and providing a large number of such biological samples. Each storage unit 1 comprises a main footprint 2 and multiple storage compartments 3, which are at least partially separated from one another by intermediate walls 4 and are enclosed by a peripheral frame 5. In addition, the intermediate walls 4 and the peripheral frame 5 are situated essentially perpendicularly to the main footprint 2 and these storage compartments 3 have both a first opening 6 and also a second opening 7. The storage compartments 3 according to the present invention are tailored to the shape of biopsy cassettes 8 or glass slides 30. This use provides that each biopsy cassette 8 or each glass slide 30 is inserted through the first opening 6 or the second opening 7 into a storage compartment 3, which has retention means 9 which prevent the inserted biopsy cassettes 8 or the inserted glass slide 30 from falling out through the first opening 6 and/or the second opening 7.

For the robotic handling and warehousing of these storage units 1, they preferably have a main footprint 2, which at least approximately corresponds to the SBS standard footprint of a standard microplate. One or more of these biopsy cassettes 8 or glass slides 30 may be removed robotically and automatically from the corresponding storage compartments 3 of a first storage unit 1 and inserted into selected storage compartments 3 of a second storage unit 1 or a collection unit. Preferably, two of these storage units 1 are situated one above the other in register and displaced in relation to one another using a device 22 of a transfer system 21, biopsy cassettes 8 or glass slides 30 being pushed, vertically from the upper storage unit 1 into the storage unit 1 or collection unit lying underneath using a manipulator 23 of this transfer system 21.

Combinations and variations of the lamellae 10, cushions 11, and guide lamellae 19 shown and/or described are included in the scope of the present invention.

List of reference numerals:

| | |
|---|---|
| 1 | storage unit |
| 2 | main footprint |
| 3 | storage compartments |
| 4 | intermediate walls |
| 5 | peripheral frame |
| 6 | first opening |
| 7 | second opening |
| 8 | biopsy cassette |
| 9 | retention means |
| 10 | lamellae |
| 11 | cushions |
| 12 | support surfaces |
| 13 | vertical surfaces |
| 14 | face (14a, 14b) |
| 15 | transverse axis |
| 16 | longitudinal axis |
| 17 | bearing surfaces |
| 18 | middle wall |
| 19 | guide lamellae |
| 20 | secondary footprint |
| 21 | system |
| 22 | device |
| 23 | manipulator |
| 24 | identifier |
| 25 | warehouse unit |
| 26 | robot |
| 27 | cover |
| 28 | cage |
| 29 | hinge |
| 30 | glass slide |
| 31 | longitudinal edge |
| 32 | surface |
| 33 | slots |
| 34 | tab |
| 35 | pin |
| 36 | floor |
| 37 | dead-end space |
| 38 | grip areas |
| 39 | recesses |
| 40 | pushing surfaces |

What is claimed is:

1. A storage unit (1) for biological samples, having an essentially horizontal main footprint (2) and multiple storage compartments (3), which are at least partially separated from one another by intermediate walls (4) and are enclosed by a peripheral frame (5), the intermediate walls (4) and the peripheral frame (5) being part of the storage unit (1) and being situated essentially perpendicularly to the main footprint (2), and the storage compartments (3) having both a first opening (6) and also a second opening (7), wherein the storage compartments (3) are tailored to the shape of a biopsy cassette (8) or to the shape of a glass slide (30), so that a biopsy cassette (8) or a glass slide (30) is insertable into a storage compartment (3) through the first opening (6) and the second opening (7), and wherein the storage compartments (3) comprise retention means (9), which prevent the essentially vertically standing biopsy cassettes (8) or glass slides (30), from falling out through the first opening (6) as well as from falling out through the second opening (7), and said retention means (9) being implemented as keeping open the first opening (6) and the second opening (7).

2. The storage unit (1) according to claim 1,
wherein the storage compartments (3) have an essentially rectangular cross-section and are each implemented to receive, in relation to the main footprint, one biopsy cassette (8) standing (2) on a front face (14) or one glass slide (30) standing on a longitudinal edge (31), for biological samples.

3. The storage unit (1) according to claim 1,
wherein the storage compartments (3) have an essentially rectangular cross-section and are each implemented to receive, in relation to the main footprint (2), one biopsy cassette (8) lying on a support surface (12) or one glass slide (30) lying on a surface (32), for biological samples.

4. The storage unit (1) according to claim 1,
wherein the retention means (9) are selected from a group, which comprises single-sided and double-sided lamellae (10) and single-sided and double-sided cushions (11).

5. The storage unit (1) according to claim 4,
which comprises lamellae (10), running essentially perpendicularly in relation to the main footprint (2) that are implemented to engage using friction lock on the support surfaces (12) or other vertical surfaces (13) of a biopsy cassette (8) inserted into a storage compartment (3).

6. The storage unit (1) according to claim 4,
which comprises lamellae (10) running essentially perpendicularly in relation to the main footprint (2) that are implemented to engage using friction lock on surfaces (32) of a glass slide (30) inserted into a storage compartment (3).

7. The storage unit (1) according to claim 4,
which comprises lamellae (10) running essentially parallel in relation to the main footprint (2) that are implemented for surfaces (32) of a glass slide (30) inserted into a storage compartment (3) to partially rest on.

8. The storage unit (1) according to claim 4,
which comprises cushions (11) that are implemented to engage using friction lock on the support surfaces (12) or other vertical surfaces (13) of a biopsy cassette (8) inserted into a storage compartment (3).

9. The storage unit (1) according to claim 8,
wherein the cushions (11) extend having essentially identical effective cross-section over essentially the entire height of the storage compartments (3).

10. The storage unit (1) according to claim 8,
wherein the cushions (11) are implemented as single-sided or double-sided and are situated in a row of storage compartments (3) on a longitudinal axis (16) running centrally and transversely to these storage compartments (3).

11. The storage unit (1) according to claim 8,
wherein the cushions (11) are implemented as single-sided or double-sided and are situated in a row of storage compartments (3) on a transverse axis (15) running centrally and longitudinally to these storage compartments (3).

12. The storage unit (1) according to claim 10,
wherein the double-sided cushions (11) of a row of storage compartments (3) are situated on two longitudinal axes (16) running transversely to these storage compartments (3).

13. The storage unit (1) according to claim 1,
which comprises a middle wall (18) that comprises guide lamellae (19) running perpendicularly in relation to the main footprint (2), which project into storage compartments (3) situated on both sides of the middle wall (18).

14. The storage unit (1) according to claim 1,
the main footprint (2) of which at least approximately corresponding to the SBS standard footprint of a standard microplate.

15. The storage unit (1) according to claim 1,
which comprises at least one secondary footprint (20) that encloses an angle of at least approximately 90° together with the main footprint (2).

16. A transfer system (21) that comprises a device (22), using which at least two storage units (1) or at least one storage unit (1) according to claim 1 and one collection unit may be situated one above the other in register and displaced in relation to one another, which transfer system (21) additionally comprises a manipulator (23), using which a biopsy cassette (8) inserted into an individual storage compartment (3) or a glass slide (30) inserted into an individual storage compartment (3) may be pushed from one storage unit (1) into the other storage unit (1) or into the collection unit.

17. The transfer system (21) according to claim 16,
wherein the device (22) is implemented for situating the at least two storage units (1) or at least one storage unit (1) and one collection unit in essentially horizontal planes lying one above the other, and this manipulator (23) is implemented for essentially vertically pushing a biopsy cassette (8) or a glass slide (30) toward the main footprint (2) or away therefrom.

18. The transfer system (21) according to claim 16,
wherein the device (22) is implemented for situating the at least two storage units (1) or at least one storage unit (1) and one collection unit in essentially vertical planes lying one above the other, and this manipulator (23) is implemented for essentially horizontally pushing a biopsy cassette (8) or a glass slide (30) toward the main footprint (2) or away therefrom.

19. The transfer system (21) according to claim 18,
having a device (22), wherein the transfer system comprises a warehouse unit (25) for storing multiple storage units (1) according to claim 1 and a robot (26), using which such storage units (1) may be removed from the warehouse unit (25) and/or stored in this warehouse unit (25).

20. The transfer system (21) according to claim 19,
wherein the storage unit (25) comprises an array of retainers (27) having bearing surfaces (17), the bearing surfaces (17) of these retainers being implemented to be impinged by the main footprint (2) or by a secondary footprint (20) of a storage unit (1).

21. The transfer system (21) according to claim 16,
characterized in that the storage unit (1) and the biopsy cassettes (8) or glass slides (30) comprise at least one identifier (24), which is selected from RFID tags and barcodes.

22. A method for using biopsy cassettes (8) or glass slides (30) situated in individual storage compartments (3) of storage units (1) for biological samples for storing and providing a large number of such biological samples, each storage unit (1) comprising an essentially horizontal main footprint (2)

and multiple storage compartments (3), which are at least partially separated from one another by intermediate walls (4) and are enclosed by a peripheral frame (5), the intermediate walls (4) and the peripheral frame (5) being situated essentially perpendicularly to the main footprint (2), and these storage compartments (3) having both a first opening (6) and also a second opening (7), the method comprising: tailoring the storage compartments (3) to the shape of biopsy cassettes (8) or to the shape of glass slides (30), and inserting one biopsy cassette (8) or one glass slide (30) through the first opening (6) or the second opening (7) into such a storage compartment (3), which comprises retention means (9) that prevent the inserted biopsy cassette (8) or the inserted glass slide (30), in its essentially vertically standing storage position, from falling out of the first opening (6) and/or the second opening (7).

23. The method according to claim 22, the storage units (1) having an SBS standard footprint of a standard microplate, wherein one or more of these biopsy cassettes (8) or glass slides (30) is/are robotically removed from the corresponding storage compartments (3) of a first storage unit (1) and inserted into selected storage compartments (3) of a second storage unit (1) or a collection unit.

24. The method according to claim 23,
wherein two of the storage units (1) are situated one above the other in register and displaced in relation to one another using a device (22) of a transfer system (21), biopsy cassettes (8) or glass slides (30) being pushed vertically from the upper storage unit (1) into the storage unit (1) or collection unit lying underneath using a manipulator (23) of this transfer system (21).

* * * * *